(12) United States Patent
Millard et al.

(10) Patent No.: US 6,267,762 B1
(45) Date of Patent: Jul. 31, 2001

(54) DEVICE FOR THE POSITIONING OF A PROXIMAL EXTREMITY OF A TIBIA AGAINST A CUTTING GUIDE INCLUDING AN ADJUSTING HANDLE

(75) Inventors: Thierry Millard, Le Puits des Mezes; Jean-François Biegun, Chaumont, both of (FR)

(73) Assignee: Aesculap (FR)

( * ) Notice: Subject to any disclaimer, the term of this patent is extended or adjusted under 35 U.S.C. 154(b) by 0 days.

(21) Appl. No.: 09/535,763

(22) Filed: Mar. 28, 2000

(30) Foreign Application Priority Data

Apr. 1, 1999 (FR) .................................................. 99 04089

(51) Int. Cl.[7] .................................................. A61B 17/56
(52) U.S. Cl. .............................. 606/54; 606/56; 606/57; 606/88; 606/86
(58) Field of Search .................................. 606/53, 54, 55, 606/56, 57, 58, 59, 86, 87, 88, 80, 96, 97, 98

(56) References Cited

U.S. PATENT DOCUMENTS

| | | | |
|---|---|---|---|
| 5,628,749 | * | 5/1997 | Vendrely et al. ...................... 606/88 |
| 5,628,750 | * | 5/1997 | Whitlock et al. ...................... 606/88 |
| 5,643,272 | * | 7/1997 | Haines et al. .......................... 606/88 |
| 5,968,043 | * | 10/1999 | Ross, Jr. et al. ....................... 606/54 |
| 6,090,114 | * | 7/2000 | Matsuno et al. ....................... 606/86 |

\* cited by examiner

*Primary Examiner*—Pedro Philogene
(74) *Attorney, Agent, or Firm*—Renner, Kenner, Greive, Bobak, Taylor & Weber

(57) ABSTRACT

Equipment for the positioning of a proximal extremity of a tibia against a cutting guide (1), including a support bracket is shown. Devices are provided for distally immobilizing a tibia, which will immobilize the distal extremity of a tibia in a given position. These devices are mounted on the support bracket and can slide and be blocked in position following two directions perpendicular to the support bracket. It also includes devices (8, 9, 10, 11, 12, 13, 14) for proximally immobilizing a tibia which are mounted and can slide along the support bracket, a cutting guide (1) mounted on the support bracket frame, a gun handle (32) fixed to the support bracket, the hammer of which acts on devices (6) that enable the adjustment of the relative position of devices (8, 9, 10, 11, 12, 13, 14). This provides proximal immobilization with regard to the support bracket, the trigger of which acts on devices that enable the adjustment of the angle (posterior slope) between the support bracket and the tibia in the sagittal plane.

8 Claims, 3 Drawing Sheets

DEVICE FOR THE POSITIONING OF A PROXIMAL EXTREMITY OF A TIBIA AGAINST A CUTTING GUIDE INCLUDING AN ADJUSTING HANDLE

BACKGROUND OF THE INVENTION

1. Field of the Invention

The present invention relates to a device for the positioning of a proximal extremity of a tibia against a cutting guide, so that the cutting guide can guide a saw blade in cutting the tibia following a given resection plan, in order to install a knee prosthetic.

2. Description of the Related Art

Devices for positioning of this type are already known from the former art. They generally include a support bracket and means of distally immobilising a tibia In a given position, where those means are implemented so that they may slide along the support bracket and be securely held in place, following at least one direction, preferably two perpendicular directions, within a perpendicular plane. They also generally include means of proximally immobilising a tibia in a given position, where those means are implemented so that they may slide longitudinally along the support bracket Finally, they also include a cutting guide implemented on the support bracket.

These devices known from the former art feature several inconveniences,

The chosen resection plan takes into account the inclination of the tibia in both the ante-posterior plane as well as the inclination of the tibia in the frontal plane. When positioning the cutting guide with regard to the immobilised tibia, it is therefore necessary to be able to adjust the angle between the support bracket and the tibia within the sagittal plane (posterior slope) and also the angle between the support bracket and the tibia within the frontal plane (varus valgus). However, in order for these adjustments, as well as adjusting the height of the cutting guide to take place, these devices known from the former art consist of a great number of assembling components, complicated and difficult to manipulate.

BRIEF SUMMARY OF THE INVENTION

The invention aims to remedy those inconveniences, notably with a positioning device of the type described previously, which would be easier to grasp and manipulate, especially when adjusting the inclination of the tibia within the frontal and posterior planes and also when adjusting the height of the cutting guide with regard to the tibia.

The device for positioning the proximal extremity of a tibia with regard to a cutting guide according to the invention, is characterised in that it includes a gun handle with a hammer and a trigger fixed to the support bracket. The hammer acts on devices that allow the adjustment of the relative position of the immobilising devices with regard to the support bracket, with the possibility of blocking. The trigger acts on devices that allow the adjustment of the angle (posterior slope) between the support bracket and the tibia within the sagittal plane.

As a gun handle with a-hammer and a trigger is implemented, the device enables the surgeon to position the tibia with regard to the cutting guide in a simple manner. The positioning of proximal immobilising devices is simply done by the use of the hammer and sliding those devices along the support bracket, once the appropriate position has been reached, the hammer is released, which then blocks the proximal immobilising devices in place with the chosen resection plan facing the cutting guide. The trigger is depressed next which enables the adjustment of the posterior slope of the tibia and then released to block the adjusted value of the posterior slope. Finally, without using neither the hammer nor the trigger, the handle is used to adjust the angle of (varus valgus) by sliding within the frontal plane.

According to an aspect of the present invention, the devices that adjust the angle between the tibia and the support bracket in the sagittal plane consist of a lever, an extremity of which co-operates with a pushing component, the inferior extremity of which features gears which themselves couple with the gears of a supporting arm. The action of depressing the trigger de-couples the gears of the pushing component from the gears of the supporting arm and by releasing the trigger, couples those same gears in order to adjust the angle between the support bracket and the tibia in the sagittal plane. The device according to this improvement is of a simple assembly.

According to a further aspect of the present invention, the supporting arm includes a plate which slides within a rail that is formed within a support of the distal immobilising devices of the tibia. The sliding action takes place with the possibility of blocking by way of the co-operation between an ergot and regularly spaced notches that have been implemented on the guiding rail. The notches successively receive the ergot to enable the blocking of the plate with regard to the distal immobilising devices in order to adjust the angle between the tibia and the support bracket within the frontal plane (angle of varus/valgus).

According to a further aspect of the present invention, the proximal immobilising devices of the tibia include a stem which can slide within the support bracket, and which includes notches that couple with gears of a first pushing piece, the moving of which is acted by the hammer. Depressing of the hammer de-couples the gears of the piece from the notches of the stem, so that the stem may slide with regard to the support bracket. Suspending the action of depressing the hammer couples the gears of the piece with the notches, so that the stem is blocked in place with regard to the support bracket, therefore the proximal immobilising devices with regard to the tibia is blocked into place.

According to a further aspect of the present invention, the number of notches on the supporting arm relates to a pre-determined bracket of adjustment, based on the angle of the posterior slope, ie between zero degrees and eight degrees.

According to a further aspect of the present invention, the number of notches on the guiding rail relates to a predetermined bracket of adjustment, based on the angle of varus valgus, ie between three degrees and minus three degrees.

According to a further aspect of the present invention, the cutting guide may slide vertically with regard to the support bracket and, being blocked as for rotation, do so independently from the proximal immobilising devices. This enables an even finer adjustment of the position of the cutting guide, therefore a finer adjustment of the position is obtained for the resection of the tibia.

DETAILED DESCRIPTION OF THE INVENTION

Figure 1:
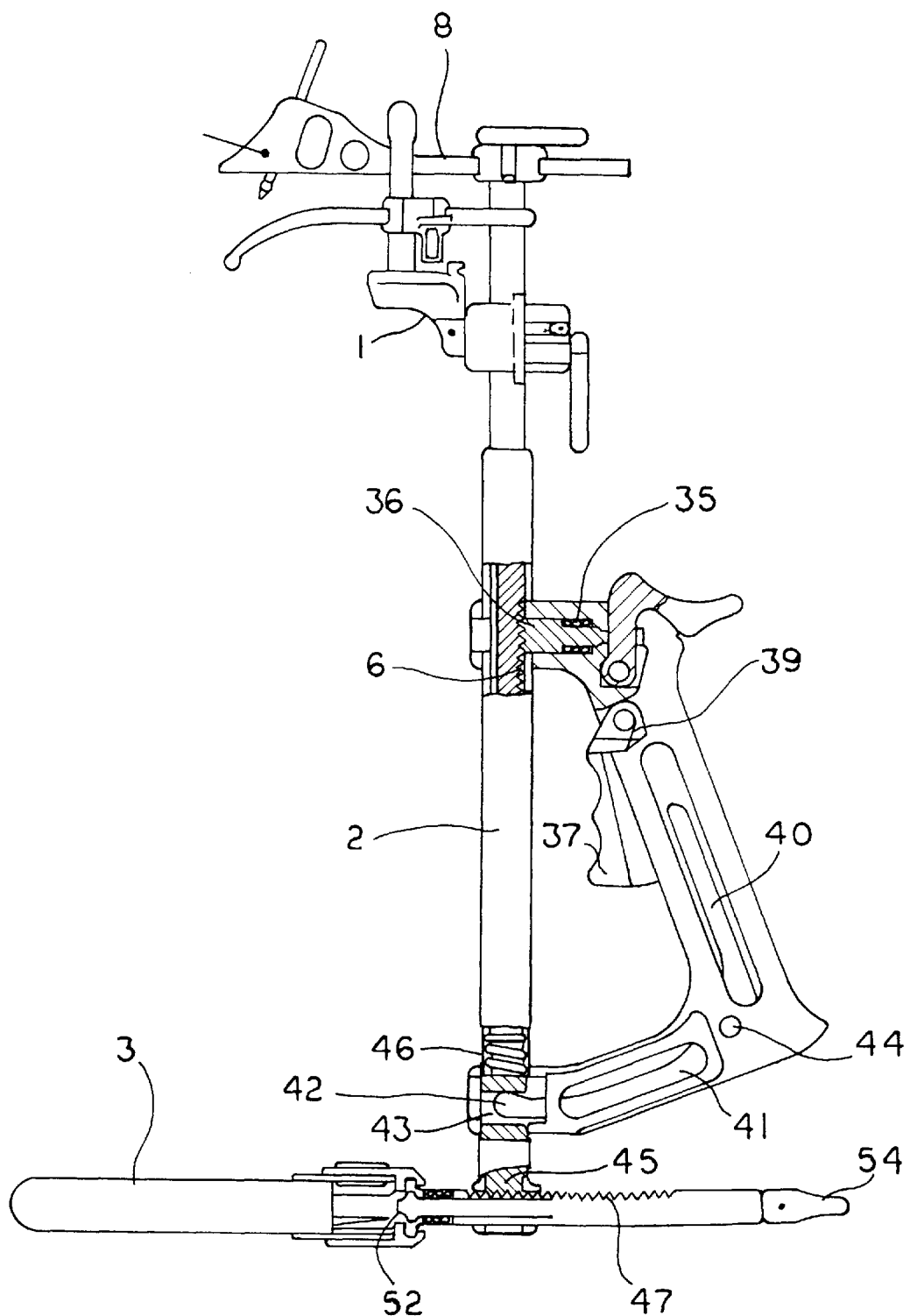
FIG. 1 is a side representation of a device according to the present invention.
Figure 2:
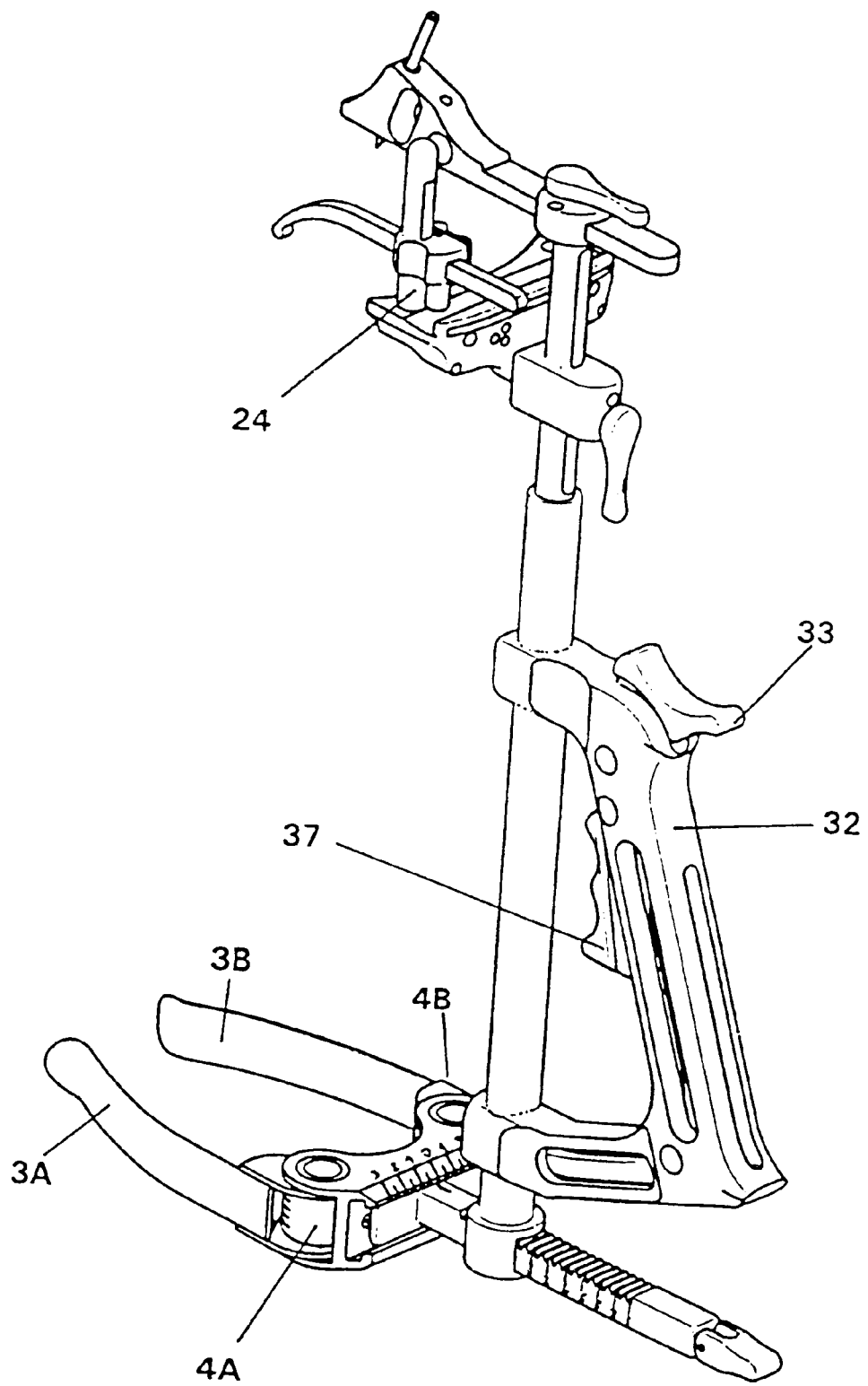
FIG. 2 is a representation in perspective of a device according to the present invention.
Figure 3:
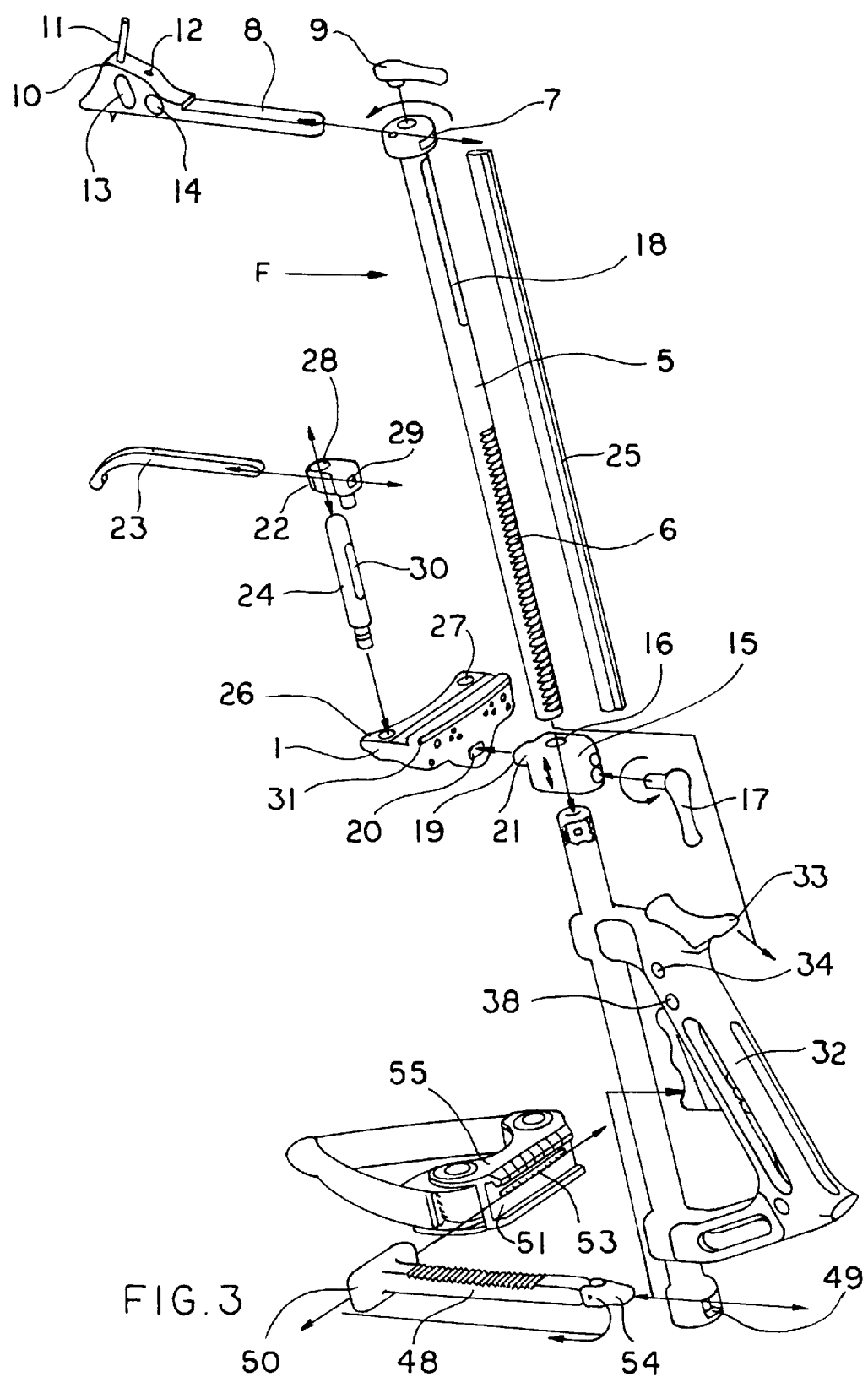
FIG. 3 is a representation in perspective of the device according to FIG. 1, with the various elements the device consists of being disassembled to allow for a better comprehension of the Figure.

In FIG. 1, the device for the positioning of a proximal extremity of a tibia (not represented) against a cutting guide I includes an oblong, cylindrical support bracket 2. A claw 3 consists of two forks 3A and 3B, which clamp the tibia (malleol), two springs 4A and 4B which co-operate with the two forks to grip the tibia and is articulated on a support 55. The claw 3 is mounted on the support bracket 2 so that it may slide perpendicularly to the plane including the tibia and the support bracket (the sagittal plane). The support bracket which is hollow and of oblong shape 2 features a stem 5, which slides in the upper part of the support bracket 2. This sliding stem 5 includes notches 6 on its lower extremity, which enable the positioning of stem 5 with regard to support bracket 2 and blocking in position, as will be explained later. The upper part of stem 5 includes a bore 7 with a rectangular transversal section, which accommodates a fixating rod 8 sliding within this bore 7 and which can be blocked in any chosen position by a screw 9. The fixating rod 8 Includes a cylindrical bore 10, which accommodates a pin 11 that will be punched to the proximal part of the tibia, notably to the tibia needles, in order to fix it. Another bore 12 is also included for another broach or pin. Two hollow notches 13 and 14 are implemented within the rod 8 to lighten it and therefore lightens the weight of the entire device. A support 15 for the cutting guide can slide on the upper part of stem 5. This sliding action takes place independently from the sliding action of stem 5 within support bracket 2. The support 15 features a bore 16 through which stem 5 passes and through which support 15 can slide on stem 5. A screw 17 enables the blocking of support 15 of the cutting guide on stem 5 in the appropriate position. The rotation of support 15 with regard to the longitudinal axis of stem 5 is prevented by the implementation of a longitudinal slot 25 on stem 5, through which support 15 can slide, and an ergot in support 15, so that support 15 may not rotate on stem 5. The cutting guide 1 is fixated to support 15 in a simple manner, for instance by way of the co-operation of a small plate 19 and a bore 20 of the cutting guide, which features a complementary transversal section, with separable coupling. To this effect the small plate 19 features a transversal orifice 21 for the reception of a hollow stem which contains a spring that pushes a retaining ball outward. This ball lodges itself in a corresponding notch implemented in the surface of the bore 20 of the cutting guide Therefore, in order to mount the cutting guide onto the small plate or dismount it from the small plate, the two elements may simply be manually moved away from one another so that the ball is forced inside the orifice 21, as the ball juts outward either when both elements are separate or when the cutting guide is coupled to the small plate 19. The cutting guide includes, in its upper part, a removable palpating device including a body 22, a palpating rod 23 and a column 24. The column 24 inserts in the cutting guide 1 in a left-hand bore 26 or a right-hand bore 27. A ball-based coupling system can be implemented. The body 22 slides on column 24 by way of a bore 28, whereas the palpating rod 23 slides in a bore 29 transversal to bore 28.

The sliding action of the body 22 on column 24 can take place without a mutual rotation. The transversal section of bore 28 may indeed be circular and complementary to that of column 24, but the co-operation of the rod 23 with the opening 30 prevents any rotation of the body 22. Similarly, the sliding action of the rod 23 takes place without any possible rotation as the transversal section of bore 29 Is square, as is that of rod 23. An opening 30 is implemented in column 24 that will allow rod 23 to pass through it. Both the rod 23 and the body 22 are blocked onto column 24 by pressing part of body 22 onto column 24. This is achieved by way of a spring positioned inside the body 22. The palpating rod can therefore materialise a height for the resection of the tibia.

The cutting guide 1 includes a slot or guide 31 implemented for the passing of a saw blade, A gun handle 32 is implemented on support bracket 2. In its upper part, this gun handle 32 includes a hammer 33 articulated to a rotational axis 34 and which cooperates with a spring 35, which itself actions a first pushing piece 36. The extremity of the piece 36 proximal to the spring 35 includes gears that can couple with the notches 6 of stem 5. The gun handle 32 also include a trigger 37 articulated to a rotational axis 38. A spring 39 exerts a rappelling action on the trigger 37 with regard to the rotational axis 38. The trigger 37 co-operates with a lever 40 placed inside the gun handle 32. This lever 40 is bent and incorporates two branches, a first branch which co-operates with the trigger 37 and a second branch 41, which penetrates a transversal bore 43 of support bracket 2 in its lower part, by way of its extremity 42. The lever 40 is permanently mounted inside the handle 32 and is articulated to an axis 44, itself situated at the junction where both branches of lever 40 meet. Within the lower part of support bracket 2, the extremity 42 of lever 40 co-operates with a second pushing piece 45 and a rappelling spring 46, which are both situated and can slide inside support bracket 2. The lower extremity of the second pushing piece 45 features gears which can couple with notches 47 of an oblong supporting arm 48. Itself of a square transversal section and which can slide In a bare 49 of support bracket 2 in its lower part. The bore 49 has a square transversal section, complementary to the square transversal section of supporting arm 48. The sliding action takes place in the mid-lateral plane. This supporting arm 48 includes a guiding plate 50 at one of its extremities, which can slide on a guiding rail 51 formed within the support of claws 3A and 3B. The sliding action of the guiding plate 50 takes place perpendicularly to support bracket 2 and perpendicularly to the sliding direction of the supporting arm 48 in the bore 49. The outside of plate 50 (away from support bracket 2) includes an ergot 52, which can couple to a row of notches 53 which are implemented on the side of the guiding rail 51 onto which plate 50 is guided. The ergot 52 can couple to each notch 53 by being pushed into place by way of a spring inside supporting arm 48. The position of the support of claws 3A and 3B varies for each position of the ergot 52 in a notch 53 and therefore the relative angle between the tibia held by the claws and the support bracket also varies in the frontal plane.

The adjustment of the position of the tibia with regard to the cutting guide takes place in following manner:

The user holds the positioning system by its gun handle 32 and grasps the bones of the tibia with the claws 3A and 3B, which tightly adapt by way of the springs 4A and 40. The user next depresses the hammer 33 with his thumb. As the hammer 33 rotates clockwise it relaxes the spring 35, which exerts its action on the first pushing piece 36, the gears of which de-couple from the notches 6. With his other hand, the user can then adjust the height of stem 5 by sliding it within support bracket 2. Once the appropriate height for the fixating rod 8 is reached, the user then releases the hammer 33 which, through spring 35, couples the pushing piece 36 back by way of coupling its gears to notches 6 of stem 5. The stem 5 is then blocked in place and cannot slide within support bracket 2 any further. After releasing the hammer, the user then fixes the upper part of the tibia (needles) by way of the pin 11, at the level of the centre of the tibia. He then depresses the trigger 37. The pushing action on this trigger 37 acts on the first branch of lever 40 linked to trigger 37 and makes the second branch 41 of lever 40 lift up. The extremity 42 of the second branch 41 of lever 40 therefore pulls the second pushing piece 45 upwards, the gears at the lower extremity of which de-couple from gears 47 of the supporting arm 48. The supporting arm 48 can now slide in bore 49 perpendicularly to support bracket 2. When the appropriate value setting for the angle in the sagittal plane between the tibia, held in place by its bones in claws 3A and 3B, and support bracket 2 is reached, the user then release the trigger 37. The trigger 37 is then brought back to its free position by the rappelling action of spring 39. The extremity 42 of the second branch 41 of lever 40 then lowers and the gears of the pushing piece 45 couple again with the gears 47 of the supporting arm 48. The posterior slope of the tibia is therefore set with regard to the support bracket. The angle may be chosen between zero degrees and eight degrees, so an appropriate number of gears 47 should be planned to accommodate this range. The angle of varus valgus (in the frontal plane) is then set by way of sliding the plate 50 on its guiding rail 51, by way of moving the support bracket 2 by the handle 32 perpendicularly to FIG. 1 (frontal plane). Once the appropriate angle has been chosen, the ergot 52 is placed in the notch 53 within which it should rest by now, by way of a lever 54. The varus valgus is then set. The number of notches 53 is planned to allow for adjustments of ±three degrees of the varus valgus angle (frontal plane). As the height, posterior slope and varus valgus angle have all been set, the palpating rod 23 is set next. The palpating rod slides along the column 24 to define the height of the resection plan exactly. The resection can then take place. The support 15 of the cutting guide can be slid to bring the palpating rod 23 in contact with the bone so as to precisely materialise the resection plan and block the support 15 in position by way of the screw 17.

The hammer and the trigger are both integrated to the handle. The user can easily depress the hammer with his thumb and the trigger with his index for all the relative positions of the proximal immobilising devices with regard to the support bracket.

In the former art, notably in French patent 2.720.629, the trigger is independent of the handle and, for certain relative positions of the proximal immobilising devices with regard to the support bracket, the user will not have an index finger long enough to use the trigger and simultaneously use the hammer with his thumb.

According to a preferred implementation of the invention, devices to transmit the action of the finger on the trigger to the adjusting devices of the angle between the support bracket and the tibia are planned, but those devices do not form part of the support bracket.

According to a preferred implementation of the invention, these devices consist of at least one lever, which is situated outside the support bracket and inside the gun handle.

What is claimed is:

1. A device for the positioning of a proximal extremity of a tibia against a cutting guide including:
    a support bracket;
    means for distally immobilizing a tibia, which immobilize the distal extremity of a tibia in a given position and are mounted on the support bracket, and can slide and be blocked in position, following at least one direction perpendicular to the support bracket;
    means for proximally immobilizing a tibia, which are mounted and can slide on the support bracket;
    a cutting guide mounted on the support bracket, wherein a handle including a hammer and a gun trigger are mounted on the support bracket, the hammer of which acts on devices that enable the adjustment of the relative position of devices for proximal immobilization with regard to the support bracket with the possibility of blocking those in place and the trigger of which acts on devices that enable the adjustment of the angle (posterior slope) between the support bracket and the tibia in the sagittal plane.

2. A device for the positioning of a proximal extremity of a tibia against a cutting guide according to claim 1, wherein the devices which enable the adjustment of the angle between the tibia and the support bracket in the sagittal plane includes a lever, an extremity of which cooperates with a pushing piece, the inferior extremity of which includes gears that couple with the notches of a supporting arm, wherein the pushing action against said trigger de-couples the gears of the second pushing piece from the notches of the supporting arm, and the release of the trigger couples the gears of the second pushing piece with the notches of the supporting arm, so that the angle between the support bracket and the tibia may be set in the sagittal plane.

3. A device for the positioning of a proximal extremity of a tibia against a cutting guide according to claim 2, wherein the supporting arm includes a plate sliding on a guiding rail, itself implemented on the support of the distal immobilizing devices for the tibia, and said sliding action is implemented with the possibility of blocking by way of the cooperation between an ergot and a row of notches implemented on the guiding rail, as the notches successively receive the ergot for blocking the plate with regard to the distal immobilizing devices, so as to adjust the angle between the tibia and the support bracket in the frontal plane (angle of varus/valgus).

4. A device for the positioning of a proximal extremity of a tibia against a cutting guide according to claim 1, wherein the proximal immobilizing devices for the tibia include a stem that can slide into the support bracket and includes notches, which can be coupled to the gears of a first pushing piece, the moving of which is initiated by the hammer, and the pushing of said hammer de-couples the gears of the pushing piece from the notches of the stem so that the stem can slide in the support bracket and releasing the pushing action against the hammer couples the gears of the first pushing piece with the notches to block the stem into position with regard to the support bracket, therefore blocking the proximal immobilizing devices with regard to the tibia.

5. A device for the positioning of a proximal extremity of a tibia against a cutting guide according to claim 2, wherein the proximal immobilizing devices for the tibia include a stem that can slide into the support bracket and includes notches, which can be coupled to the gears of a first pushing piece, the moving of which is initiated by the hammer, and the pushing of said hammer de-couples the gears of the pushing piece from the notches of the stem so that the stem can slide in the support bracket and releasing the pushing action against the hammer couples the gears of the first pushing piece with the notches to block the stem into position with regard to the support bracket, therefore blocking the proximal immobilizing devices with regard to the tibia.

6. A device for the positioning of a proximal extremity of a tibia against a cutting guide according to claim 2, wherein the number of notches on the supporting arm correspond to an adjustment variance of the angle of the posterior slope, for instance between zero and eight degrees.

7. A device for the positioning of a proximal extremity of a tibia against a cutting guide according to claim 3, wherein the number of notches on the guiding rail correspond to an adjustment variance of the angle of varus/valgus, for instances between minus three and three degrees.

8. A device for the positioning of a proximal extremity of a tibia against a cutting guide according to claim 1, wherein the cutting guide is mounted so as to slide but not rotate with regard to the support bracket in a vertical direction, independently of the proximal immobilizing devices.

* * * * *